United States Patent
Wu et al.

(10) Patent No.: US 7,939,567 B2
(45) Date of Patent: May 10, 2011

(54) DEXTROMETHORPHAN-BASED METHOD FOR TREATING ACNE

(75) Inventors: Hua-Lin Wu, Tainan (TW); Guey-Yueh Shi, Tainan (TW)

(73) Assignee: Blue Blood Biotech Corp., Taipei (TW)

( * ) Notice: Subject to any disclaimer, the term of this patent is extended or adjusted under 35 U.S.C. 154(b) by 0 days.

(21) Appl. No.: 11/361,589

(22) Filed: Feb. 24, 2006

(65) Prior Publication Data

US 2007/0203164 A1   Aug. 30, 2007

(51) Int. Cl.
*A01N 33/02* (2006.01)
(52) U.S. Cl. .................. 514/656; 514/859
(58) Field of Classification Search .......... 514/656, 514/859
See application file for complete search history.

(56) References Cited

U.S. PATENT DOCUMENTS

| | | | |
|---|---|---|---|
| 2,676,177 A | 4/1954 | Schnider et al. | |
| 5,206,248 A | 4/1993 | Smith | |
| 5,260,066 A | 11/1993 | Wood et al. | |
| 5,366,980 A | 11/1994 | Smith | |
| 5,834,480 A | 11/1998 | Khoury | |
| 5,994,330 A * | 11/1999 | El Khoury | 514/123 |

OTHER PUBLICATIONS

Gould, P. Salt selection for basic drugs. International Journal of Pharmaceutics, 33 (1986) 201-217.*

Maurice, Tangui et al., The interaction between neuroactive steroids and the $\sigma_1$ receptor function: behavioral consequences and therapeutic opportunities, *Brain Research Reviews* 37 (2001) 116-132.

Häfliger, O. et al., Uber ein Photooxydationsprodukt von (+)-3-Methoxy-N-methyl-morphinan, *Fasciculus VII* (1956) No. 237-238.

Wang, Chien-Chuan et al., Dextromethorphan Prevents Circulatory Failure in Rats with Endotoxemia, *Journal of Biomedical Science*, (2004) 11:739-747.

Schmitt B et al: "Treatment with the N-methyl-D-asparate receptor antagonist dextromethorphan in severe bacterial meningitis: preliminary results." European Journal of Pediactrics Oct. 1998, vol. 157, No. 10, (Oct. 1998), pp. 863-865.

Saidi R F et al: "Bacteroides fragilis toxin rapidly intoxicates human intestinal epithelial cells (HT29/C1) in vitro." Infection and Immunity Dec. 1996. vol. 64 No. 12, (Dec. 1996), pp. 5029-5034.

Supplementary European Search Report for EP 06 75 1392 (Oct. 22, 2009).

* cited by examiner

*Primary Examiner* — Sreeni Padmanabhan
*Assistant Examiner* — Renee Claytor
(74) *Attorney, Agent, or Firm* — Hsiu-Ming Saunders; Intellectual Property Connections, Inc.

(57) ABSTRACT

The present invention relates to a method for providing bactericide or bacteriostatic, especially for treating disease due to bacterial infection. The method comprising administering a patient in need of such treatment a therapeutically effective amount of a compound of dextromethorphan or naloxone or a pharmaceutically acceptable salt or an analog thereof. The compound is applied to skin or mucosal surface of the patient. The invention also relates to a method of treating inflammation caused by suppressing secretion of TNF-$\alpha$, IL-6, or MCP-1 from macrophage comprising administering a patient in need of such treatment a therapeutically effective amount of NADPH oxidase inhibitor.

11 Claims, 2 Drawing Sheets

DEXTROMETHORPHAN-BASED METHOD FOR TREATING ACNE

BACKGROUND OF THE INVENTION

Field of the Invention

The present invention relates to a method for providing bactericide or bacteriostatic. The invention also relates to a method of treating inflammation caused by tumor necrosis factor-α (TNF-α), and interleukin-6 (IL-6) or monocyte chemoattractant protein-1 (MCP-1) from macrophage.

Acne is developed in teen-agers at an incidence of 90% but also found in adults of in their twenties- or thirties at rare intervals. Acne (or acne vulgaris) is a chronic inflammatory disease or a disorder developed at sebaceous gland and hair follicle, of which etiopathology includes excess secretion of sebum, dyskeratinization of epidermis of hair follicle, overgrowth of anaerobic skin-colonizing bacterium, *Propionibacterium acnes* (*P. acnes*) and other causes. Acne is generally found on face, chest, back, neck and brachium, the most noticeable parts of skin, and characterized as comedo, pustule, lupus, petty knob or scar.

Acne afflicts millions of people worldwide. Current available therapies have a variety of disadvantages, ranging from adverse effects (such as blistering, photosensitivity, allergic reactions) in patients to a lack of or minimal effectiveness in patients (e.g. due to microbial resistance to the therapeutic agents). Accordingly, there continues to be need for an alternative therapeutic means for treating or controlling acne, particularly acne vulgaris.

As a result of bacterial growth in these horny impactions, the follicle ruptures initiating the inflammatory phase of the disease which takes the form of pustules, papules, cysts, and nodules. Although many different approaches have been used for the treatment of this affliction, none are universally effective and most possess undesirable side effects.

Dextromethorphan (DM, (+)-3-methoxy-17-methyl-9a,13a,14a-morphinan), a widely used over the counter antitussive agent, is a noncompetitive antagonist of the N-methyl-D-aspartate (NMDA) receptor and is protective against the adverse effect of Hcy (homocysteine) and its metabolites. DM, the D-isomer of the opiate agonist levorphanol, has none of the analgesic or sedative effects associated with the opiates. DM, acting as an antagonist at NMDA receptors, suppresses the transmission of nerve impulses and nerve signals mediated through NMDA receptors. In addition, DM has also been reported to suppress activity at neuronal calcium channels.

DM is an antitussive used in the treatment and relief of cough symptoms associated with upper respiratory illness such as the flu or the common cold. It is commercially available in the form of its hydrobromide salt, DM-HBr (dextromethorphan hydrobromide). The salt dissolves readily in digestive juices wherein the DM is fed into the blood stream. Biological modification and/or elimination of the medication from the body begins immediately. The usual doses for immediate release medication in the body range from about 15 to about 30 mg administered every 4 to 6 hours.

DM is a synthetic opioid. Normally the hydrobromide of DM is used pharmacologically, although other salts are not excluded. The preparation of (+)-3-methoxy-17-methyl-9a,13a,14a-morphinan was disclosed in U.S. Pat. No. 2,676,177 (Schnider et al.) and in Hafliger et al., Helv. Chil. Acta 39, 1956: 2053.

Transdermal administration of DM, but not as antitussive agent, is known, e.g. from U.S. Pat. No. 5,260,066 for cryogel bandages.

Dextromethorphan (DM) is widely used as a cough syrup, and it has been shown to be sufficiently safe in humans to allow its use as an over-the-counter medicine. It is well tolerated in oral dosage form, either alone or with quinidine, at up to 120 milligrams (mg) per day, and a beneficial effect may be observed when receiving a substantially smaller dose (e.g., 30 mg/day) (U.S. Pat. No. 5,206,248).

DM is a weak, noncompetitive NMDA receptor antagonist that binds with moderate-to-high affinity to the phencyclidine site of the receptor complex. However, DM has additional, unique pharmacological properties. Binding studies suggest it is a ligand at the high affinity sigma 1 site, where it initially was proposed to act as an antagonist but more recently as an agonist (Maurice et al., Brain Res. Brain Res. Rev., 2001; 37:116-32). Sigma ligands also modulate NMDA responses.

Chien-Chuan Wang et al. used an LPS-induced endotoxemia model in rats. In this study, they examined whether a decrease in the production of cytokine or NO in sepsis is involved in the beneficial effects of DM in animals with endotoxemia. Their results demonstrated that DM inhibits TNF-a (thus indirectly suppressing IL-10 production), NO, and the superoxide anion, resulting in mitigation of the development of detrimental effects (including circulatory failure and mortality) in LPS-induced endotoxemia in rodents. Their results indicated that DM has beneficial effects that may potentially be developed as a treatment for patients with sepsis (Wang et al., J. Biomed Sci., 2004; 11:739-747).

Naloxone (trade name Narcan) is a drug used to counter the effects of overdosing on opiates such as heroin or morphine. Naloxone has been distributed as part of emergency kits to heroine addicts, which has been shown to reduce death rates. The drug also blocks the action of pain-lowering endorphins which the body produces naturally. The likely reason for this is that these endorphins operate on the same opiate receptors.

U.S. Pat. No. 5,366,980 disclosed a method for treating human patients suffering from dermatitis, particularly severe dermatitis which does not respond adequately to non-prescription drugs. Such patients are treated using DM, an antitussive agent normally used in cough syrup. If the patient is a so-called "extensive metabolizer," an antioxidant drug (such as quinidine) can be coadministered to inhibit the DM-degrading activity of debrisoquin hydroxylase, an enzyme that will rapidly convert DM into its metabolite, dextrorphan. This treatment has been shown to be highly effective in treating severe dermatitis, and in most patients this drug combination causes no significant adverse side effects.

Use of knockout mice has implicated the chemoattractant cytokine (chemokine), monocyte chemoattractant protein (MCP-1), in attracting macrophage recruitment in atherosclerosis. Macrophage-activation stimuli associated with atherosclerotic risk factors include oxidised low density lipoprotein (oxLDL, 'bad cholesterol'), advanced glycosylation end products (AGEs) of diabetes, angiotensin II and endothelin. Substantial work has clarified macrophage activation by OxLDL via macrophage scavenger receptors (MSRs), especially MSRA and CD36. Activated macrophages express effector molecules that kill cells and degrade extracellular matrix. These include Fas-L and nitric oxide (NO). Macrophage NO is derived from the high output inducible nitric oxide synthase (iNOS) pathway and upregulates vascular smooth muscle (VSMC) cell surface Fas, priming them for apoptosis. Activated macrophages express surface Fas-L, similar to cytotoxic T-lymphocytes and natural killer cells. Since VSMCs promote plaque stability, VSMC apoptosis may promote plaque rupture. Macrophages express multiple metalloproteinases (e.g. stromelysin) and serine proteases (e.g. urokinase) that degrade the extracellular matrix, weakening the plaque and making it rupture prone.

Macrophages secrete numerous other effectors including reactive oxygen species, eicosanoids, tumour necrosis factor alpha (TNF-α), interleukin-1 (IL-1) and interleukin-6 (IL-6). Macrophage-derived transforming growth factor beta promotes fibrosis. Existing cardiovascular treatments including angiotensin II receptor antagonists and angiotensin converting enzyme inhibitors, aspirin, cholesterol reduction agents especially statins may inhibit macrophages. The interaction of NO-donors with macrophages and apoptosis is complex and bifunctional. Traditional anti-inflammatory agents such as glucocorticoids and cyclophosphamide have very serious side effects and are probably inappropriate.

SUMMARY OF THE INVENTION

The present invention provides a method for treating disease due to bacterial infection comprising administering a patient in need of such treatment a therapeutically effective amount of a bactericidal compound.

The present invention further provides a method for treating inflammatory disease caused by suppressing secretion of TNF-α, IL-6, or MCP-1 from macrophage comprising administering a patient in need of such treatment a therapeutically effective amount of NADPH oxidase inhibitor.

The present invention also provides a composition comprises a NADPH oxidase inhibitor and a bactericidal compound.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE INVENTION

Figure 1:
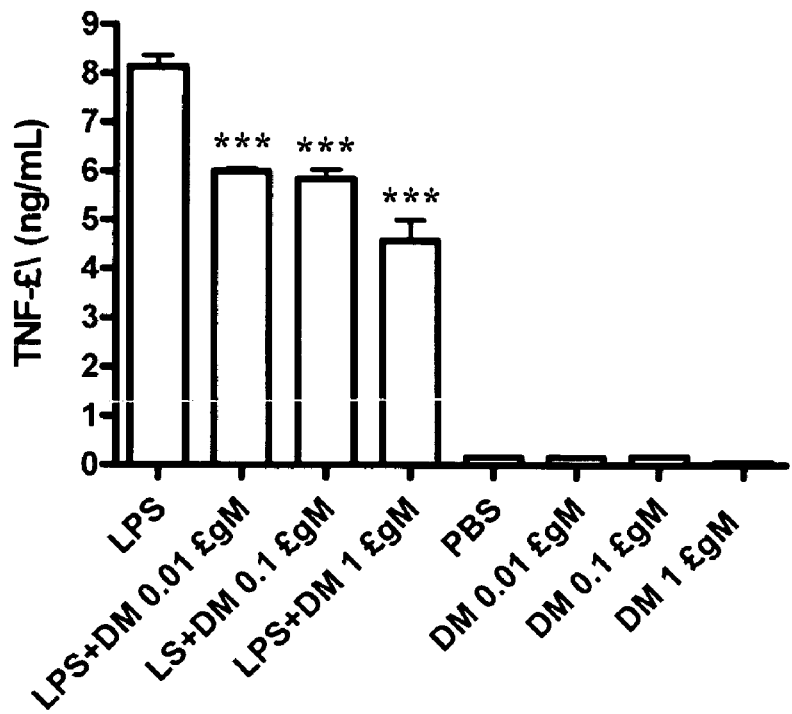
FIG. 1 shows effect of dextromethorphan treatment on the LPS-induced macrophage release of TNF-α (A) and IL-6 (B). THP-1 cell culture was pretreated for 1 hour with the indicated concentrations of dextromethorphan before stimulation with 100 ng/mL LPS. Supernatants were harvested at 24 hours for the measurement of TNF-α and IL-6. The results are expressed as mean±SD of 3 experiments.  p<0.01 and * p<0.001 are compared with the LPS-treated cultures.
Figure 1:
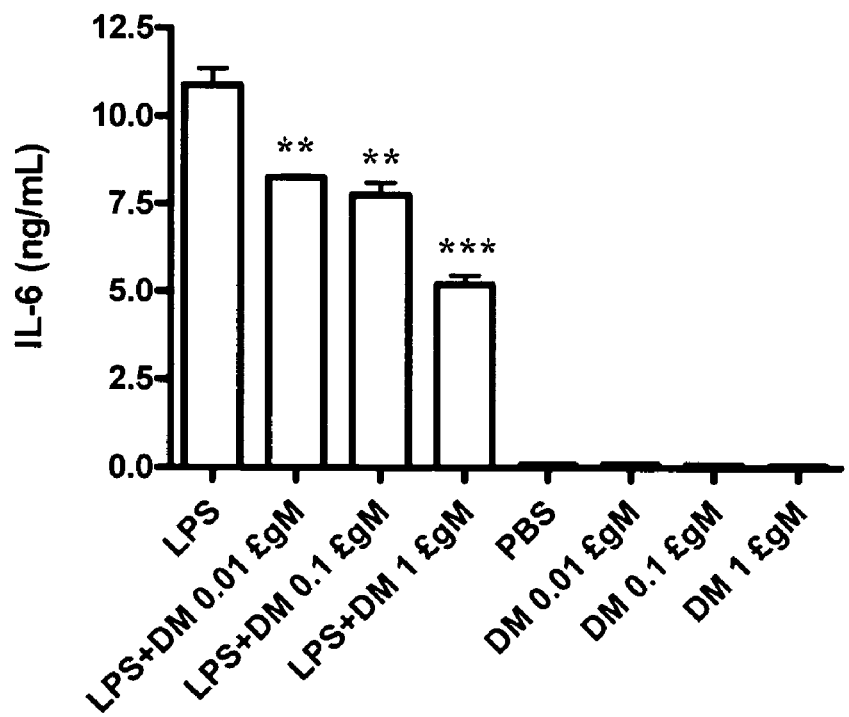

Most of diseases or disorders caused by bacterial infection involve the mass growth of the pathogen and undesired side effect such as inflammation. Although there are a lot of antibiotics to kill or inhibit pathogen growth and some drugs for treating inflammation, it could not achieve good treating performance for some trouble diseases such as acne.

The present invention shows that the substituted morphinan (such as dextromethorphan) has bactericidal and bacteriostatic activities on bacteria (such as *Propionibacterium acnes*).

Accordingly, the present invention relates to a method for treating disease due to bacterial infection comprising administering a patient in need of such treatment a therapeutically effective amount of a compound of formula I or formula □, or a pharmaceutically acceptable salt or analog thereof,

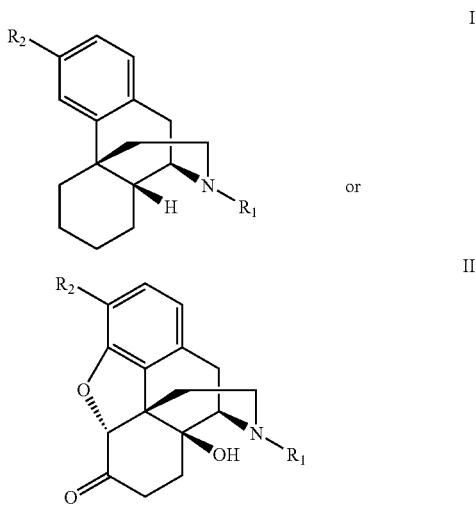

wherein
$R_1$ is $C_{1-6}$ alkyl, $C_{2-6}$ alkenyl, cyclo$C_{3-6}$ alkyl-$C_{1-6}$ alkyl, or $C_{2-6}$ alkylene and $R_2$ is H, OH, $C_{1-6}$ alkyl, $C_{1-6}$ alkoxy, $C_{2-6}$ alkenyl or $C_{2-6}$ alkylene.

The preferred salt of formula I is dextromethorphan hydrobromide or dextromethorphan phosphate. The preferred compound of formula II is 17-allyl-4,5α-epoxy-3,14-dihydroxymorphinan-6-one (naloxone) or 17-(cyclopropylmethyl)-4,5α-epoxy-3,14-dihydroxymorphinan-6-one (naltrexone). The preferred compound of formula I is (+)-3-methoxy-17-methyl-9α,13α,14α-morphinan (dextromethorphan). Most of the addictive analgesic opiates, such as morphine, codeine, and heroin, are levorotatory stereoisomers (they rotate polarized light in the so-called left-handed direction). They have four molecular rings in a configuration known as a "morphinan" structure. Many dextrorotatory analogs of morphine are much less addictive than the levorotatory compounds. Some of these dextrorotatory analogs, including dextromethorphan and dextrorphan, are enantiomers of the morphinan structure. In these enantiomers, the ring that extends out from carbon atoms 9 and 13 is oriented in the opposite direction from that depicted in the above structure.

The present invention also relates to a method for treating inflammatory disease caused by suppressing secretion of TNF-α, IL-6 or MCP-1 from macrophage comprising administering a patient in need of such treatment a therapeutically effective amount of NADPH oxidase inhibitor.

According to the method of the present invention, wherein the infectious bacteria is gram-positive or gram-negative. *Propionibacteria* are slow-growing, nonsporeforming, gram-positive, anaerobic bacteria. They can be rod-shaped or branched and can occur singularly, in pairs, or in groups. They generally produce lactic acid, propionic acid, and acetic acid from glucose. *Propionibacterium acnes* is a gram-positive bacterium that inhabits the adult human skin. It resides within sebaceous follicles, usually as a harmless commensal even though it is involved in acne formation. It is also associated with other diseases like endocarditis, corneal ulcers, among others. However, *Bacteroides fragilis*, a gram-negative rod, constitutes 1% to 2% of the normal colonic bacterial microflora in humans. It is frequently associated with extra-intestinal infections such as abscesses and soft tissue infections, as well as diarrheal diseases in animals and humans. Therefore, the better embodiment of infectious bacteria is *Propionibacterium acnes* or *Bacteroides fragilis*. The best embodiment of infectious bacteria is *Propionibacterium acnes* causes acne.

A dose of the pharmaceutical composition contains at least a therapeutically effective amount of the active compound (i.e., a compound of formula I or a pharmaceutically acceptable salt thereof), and preferably is made up of one or more pharmaceutical dosage units. The selected dose may be administered to a mammal, for example, a human patient, in need of such treatment a therapeutically effective amount of a compound of formula I or a pharmaceutically acceptable salt or an analog thereof, by any known or suitable method of administering the dose, including topically, for example, as an ointment or cream; orally; rectally, for example, as a suppository; parenterally by injection; or continuously by intravaginal, intra-nasal, intra-bronchial, intra-aural, or intra-ocular infusion. The better embodiment of the compound is applied to skin or mucosal surface of the mammals which suffered from bacteria infection. The best embodiment of the mammal is a human patient.

A "therapeutically effective amount" is intended to mean the amount of an inventive compound that, when administered to a mammal in need thereof, is sufficient to effect treatment for disease conditions alleviated by the inhibition of the activity of bacteria. The amount of a given compound of the invention that will be therapeutically effective will vary depending upon factors such as the particular compound, the disease condition and the severity thereof, the identity of the mammal in need thereof, which amount may be routinely determined by artisans.

The effective amount of the compound applied to a patient in need of such treatment is ranging from 10000 ppm to 1 ppm, preferably 5000 ppm to 1 ppm, more preferably 1000 ppm to 1 ppm and most preferably 1 ppm.

The term "pharmaceutically acceptable salt" used herein means any salt that is pharmaceutically acceptable and has the desired pharmacological properties. Such salts include salts that may be derived from an inorganic or organic acid, or an inorganic or organic base, including amino acids, which is not toxic or undesirable in anyway. Suitable inorganic salts include those formed with the alkali metals, e.g., sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane and arene-sulfonic acids such as methanesulfonic acid, benzenesulfonic acid, sulfonic acid, and phosphatic acid). When there are two acidic groups present, a pharmaceutically acceptable salt may be a mono-acid-mono-salt or a di-salt; and similarly, where there are more than two acidic groups present, some or all of such groups can be salified.

It has been found that the use of NADPH oxidase inhibitor in inflammatory disease caused by suppressing secretion of TNF-α, IL-6, or MCP-1 from macrophage.

The term "NADPH oxidase inhibitor" used herein is defined to encompass all of compounds, including pharmaceutically acceptable salts thereof, derivatives thereof, dimers thereof, and prodrugs thereof, which can be metabolically converted into an inhibitor of NADPH oxidase or oxidative burst. Any NADPH oxidase inhibitor can be used in the method of the present invention as long as it is safe and efficacious. Suitable examples of such compounds include those set forth in WO 97/19679 or in U.S. Pat. No. 6,090,851. The preferred NADPH oxidase inhibitor is a compound of formula I or formula II or a pharmaceutically acceptable salt or an analog thereof

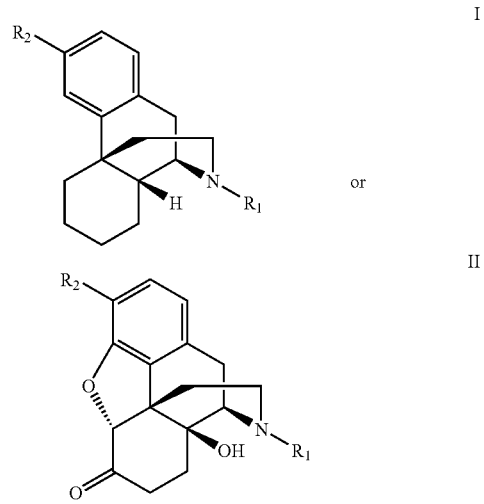

wherein
$R_1$ is $C_{1-6}$ alkyl, $C_{2-6}$ alkenyl, cyclo$C_{3-6}$ alkyl-$C_{1-6}$ alkyl, or $C_{2-6}$ alkylene and
$R_2$ is H, OH, $C_{1-6}$ alkyl, $C_{1-6}$ alkoxy, $C_{2-6}$ alkenyl or $C_{2-6}$ alkylene.

The more preferred NADPH oxidase inhibitor is (+)-3-methoxy-17-methyl-9α,13α,14α-morphinan (dextromethorphan), 17-allyl-4,5α-epoxy-3,14-dihydroxymorphinan-6-one (naloxone) or 17-(cyclopropylmethyl)-4,5α-epoxy-3,14-dihydroxymorphinan-6-one (naltrexone). The most preferred NADPH oxidase inhibitor is dextromethorphan hydrobromide or dextromethorphan phosphate.

The main role of macrophage is the removal of pathogens and necrotic debris. The latter function is more important in chronic inflammation. Macrophages also present fragments of pathogens (called antigens) that they have ingested with MHC class II molecules on their cell membranes. Helper T cells recognize this and release a lymphokine notification to B cells. The B cells then create and release antibodies specific to the particular antigen, and hence to the pathogen. Macrophages again come into play because they are especially attracted to cells with antibodies attached.

Activation of macrophage is the process of altering the morphology and functional activity of macrophages so that they become avidly phagocytic. It is initiated by lymphokines, such as the macrophage activation factor (maf) and the macrophage migration-inhibitory factor (mmif), immune complexes, c3b, and various peptides, polysaccharides, and immunologic adjuvants. The macrophage colony-stimulating factor is a glycoprotein growth factor that causes the committed cell line to proliferate and mature into macrophages.

Due to their role in phagocytosis, macrophages are involved in many diseases of the immune system. For example, they participate in the formation of granulomas, inflammatory lesions that may be caused by a large number of diseases.

Some disorders, mostly rare, of ineffective phagocytosis and macrophage function have been described. Aberrant activation of macrophage functions is associated with autoimmune diseases as well as both chronic and acute inflammatory processes.

Polymorphonuclear neutrophils (PMNs) play a major role in inflammatory diseases. They act as a first line of defense against invading infectious microorganisms. For this purpose, PMNs contain granules filled with proteolytic and other cytotoxic enzymes. Besides releasing enzymes, PMNs are also able to phagocytose and to convert oxygen into highly reactive oxygen species (ROS). Following phagocytosis, ingested microorganisms may be killed inside the phagosome by a combined action of enzyme activity and ROS production. Although the formation of ROS by stimulated PMNs is a physiological response which is advantageous to the host, it can also be detrimental in many inflammatory states in which these radicals give rise to excessive tissue damage. Therefore, there is an ongoing search for anti-inflammatory compounds which are able to prevent this damaging ROS production without affecting the other killing capacities of the PMN.

One mechanism used by PMNs to control microbes is the respiratory burst. By this mechanism molecular oxygen is converted into superoxide anions by a multi-component enzyme called the NADPH oxidase. During phagocytosis the NADPH oxidase accumulates on the phagosome membrane and superoxide anions and other ROS accumulate inside the phagosome in close proximity to ingested microbes.

It is surprisingly that some NADPH oxidase inhibitors (such as dextromethorphan) not only show anti-inflammation but could provide bactericidal or bacteriostatic activity. This effect is especially important and useful on treatment of acnes or other skin or mucosal surface.

Accordingly the present invention provides a composition comprises a NADPH oxidase inhibitor and a compound of formula I or formula II, or a pharmaceutically acceptable salt or an analog thereof

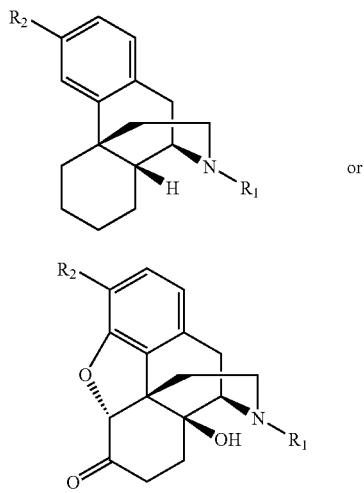

wherein
$R_1$ is $C_{1-6}$ alkyl, $C_{2-6}$ alkenyl, cyclo$C_{3-6}$ alkyl-$C_{1-6}$ alkyl, or $C_{2-6}$ alkylene,
$R_2$ is H, OH, $C_{1-6}$ alkyl, $C_{1-6}$ alkoxy, $C_{2-6}$ alkenyl or $C_{2-6}$ alkylene, and pharmaceutically acceptable carrier.

In a preferred embodiment, both NADPH oxidase inhibitor and a compound of formula I are directed to (+)-3-methoxy-17-methyl-9α,13α,14α-morphinan (dextromethorphan), 17-allyl-4,5α-epoxy-3,14-dihydroxymorphinan-6-one (naloxone) or 17-(cyclopropylmethyl)-4,5α-epoxy-3,14-dihydroxymorphinan-6-one (naltrexone).

The composition of the present invention could be made in the form of cream, ointment, lotion, mineral oil, cosmetics, shampoo, anti-itch cream, skin patch, or other things spread on epidermal or transdermal administration.

The method of the present invention can be used for wound healing, which is selected from the group consisting of incisions, lacerations, abrasions, puncture wounds, blisters, skin tears, donor or graft sites, cut wound, burn wound or radiation wound.

The examples below are non-limiting and are merely representative of various aspects and features of the present invention.

EXAMPLE

Example 1

Antimicrobial Effect on *Propionibacterium acnes* (Anaerobic Gram-Positive Bacteria) of DM Prepared DM stock solution in 500,000 ppm (50%). Added 0.25 g DM into 250 µl DMSO and stirred until mixed well. Then serial diluted 500,000 ppm DM. Centrifuged 5 ml *Propionibacterium acnes* in RCM (Reinforced Clostridial Medium) culture. Adjusted concentration of bacteria cell in medium by 20 times dilution about $OD_{595}=0.1\times10^6$ CFU/ml. Dispersed 200 µl bacteria cell in medium in aliquot to each 96-well plate. Mixed medium including bacteria cell and 2 µl DM, triplicate tests at each concentration. Bacteria cultured under anaerobic at 37° C. for 96 hours and measured the value at $OD_{595}$. MIC meant the lowest concentration of anti-bacterial agent that sufficient to suppress the growth of bacteria (e.g. growth inhibition).

Spread 0.1 ml medium including bacteria cells which $OD_{595}$ value was about $0.1\times10^6$ CFU/ml onto RCM agar plate. Pasted 0.8 cm filter paper and dropped 20 µl of DM into it. Bacteria were cultured under anaerobic at 37° C. for 96 hours and the size of the antibiotic circle was measured.
Result

TABLE 1

MIC test of *P. acnes* (Minimal Inhibit Concentration test, Unit of DM tested are expressed as ppm and percentage %)

| | DM (ppm) | | | | | | |
|---|---|---|---|---|---|---|---|
| | 5000 | 2500 | 1250 | 1000 | 500 | 250 | 125 |
| DM Percentage (%) | 0.5 | 0.25 | 0.125 | 0.1 | 0.05 | 0.025 | 0.0125 |
| Growth Inhibition | + | + | + | + | + | — | — |

(+: Growth Inhibition; —: No Growth Inhibition)

TABLE 2

Result of DM disc diffusion on anaerobic bacterial growth
inhibition: bacterial lawn strain *P. acnes* under anaerobic
condition at 37° C. for 96 hours

| Disc No. | Conc. of DM | Diameter of clear zone |
|---|---|---|
| 5 | 5% DM | 34 mm |
| 6 | 2.5% DM | 12 mm |
| 7 | 1.25% DM | — |
| 8 | 0.1% Triclosan | 30 mm |

Example 2

Antimicrobial Effect on *Bacteroides fragilis*
(Anaerobic Gram Negative Bacteria) of DM

*Bacteroides fragilis* growing in 18-24 hours in the anaerobic thioglycollate broth was used to formulate the suspension of bacteria cells of McFarland 0.5. Diluted 0.5 g/ml DMSO stock solution with anaerobic Thioglycollate broth. Added 1000 µl anaerobic Thioglycollate broth into 1000 µl of DM diluent with 1:1 ratio, and then put into the anaerobic incubator to incubate for 24 h.

TABLE 3

MIC test of *B. fragilis* (Minimal Inhibit Concentration test,
Unit of DM tested are expressed as ppm and percentage %)

| | DM (ppm) | | | | | Negative Control |
|---|---|---|---|---|---|---|
| | 5000 | 2500 | 1250 | 1000 | 500 | |
| DM Percentage (%) | 0.5 | 0.25 | 0.125 | 0.1 | 0.05 | |
| Growth Inhibition | + | + | + | — | — | — |

(+: Growth Inhibition; —: No Growth Inhibition)
"Negative Control" means Thioglycollate broth plus bacteria with no DM.

Example 3

Anti-Bacterial Effect on Aerobic Gram-Negative
Bacteria *E. coli* of DM

Base for antimicrobial disk diffusion Susceptibility Testing is made of Mueller Hinton II agar obtained from Becton, Dickinson and Company, France.

Prepared Mueller-Hinton-II-agar by suspending 38 g of the powder in 1L of double-distilled water. Autoclaved the agar at 121° C. for 15 min. t The agar was poured into each agar plate and waited for solidifying. *E. coli* of $1 \times 10^5$ CFU in 100 µl medium was spread on to the agar plate and were grown for 96 hours.

TABLE 4

Result of DM disc diffusion on aerobic Gram-negative
bacterial growth inhibition: bacterial lawn strain
*E. coli* at 37° C. for 96 hours.

| Conc. of DM | Diameter of clear zone |
|---|---|
| 10% DM | 18 mm |
| 5% DM | 13 mm |
| 2.5% DM | 9.5 mm |
| 1.2% DM | — |

Example 4

Anti-Bacterial Effect on Gram-Positive Bacteria
*Staphylococcus aureaus* of DM

Based for antimicrobial disk diffusion Susceptibility Testing is Mueller Hinton II agar obtained from Becton, Dickinson and Company, France.

Prepared Mueller-Hinton-II-agar by suspending 38 g of the powder in 1L of double-distilled water. Autoclaved the agar at 121° C. for 15 min. The agar was poured into each agar plate and waited for solidifying. *S. aureaus* of $10^5$ CFU in 100 µl medium were spread on the agar plate and were grown for 96 hours.

TABLE 5

Result of DM disc diffusion on aerobic bacterial growth inhibition:
bacterial lawn strain *S. aueaus* at 37° C. for 96 hours.

| Conc. of DM | Diameter of clear zone |
|---|---|
| 10% DM | 14 mm |
| 5% DM | 10 mm |
| 2.5% DM | — |
| 1.2% DM | — |

Example 5

Methods and Results

The monocytic THP-1 cells were cultured and differentiated into macrophages. The macrophages were pretreated with various concentrations of Dextromethophan or naloxone for 1 hour and subsequently incubated with lipopolysaccharide (LPS) for 24 hours. Dextromethophan or naloxone pretreatment significantly reduced the concentration of tumor necrosis factor-α (TNF-α), interleukin-6 (IL-6) and monocyte chemoattractant protein-1 (MCP-1) in the medium of THP-1 cells after LPS stimulation.

Preparation for Material

RPMI 1640 medium, phorbol 12-myristate-13-acetate (PMA), LPS (*Escherichia coli* 0111:B4) and naloxone were purchased from Sigma. The human THP-1 monocytic cell line was purchased from Food Industry Research and Development Institute, Hsin Chu, Taiwan. Levels of tumor necrosis factor-α (TNF-α), interleukin-6 (IL-6) and monocyte chemoattractant protein-1 (MCP-1) in medium were determined with monoclonal antibody based ELISA kits purchased from R&D Systems (Minneapolis, Minn., USA), and all animal experiments were approved by the Institutional Animal Care and Use Committee.

Cell Culture

The THP-1 cells were grown in RPMI-1640 medium containing 10% fetal bovine serum at 37° C. in 5% $CO_2$. The cells were differentiated to macrophages after treatment with 100 nM PMA to the culture for 24 hours. The cell suspension ($5 \times 10^5$) was added in 0.5 mL into each well of the tissue culture plates. LPS was dissolved in sterile water and stored at −70□ in aliquots. In treatment group, the THP-1 cell culture was pretreated for 1 hour with various concentrations of dextromethorphan or naloxone and followed by treatment with 10 μg/mL LPS for up to 24 hours. In control group, the cell culture was only treated with 10 μg/mL LPS for 24 hours. The supernatants were harvested. The levels of TNF-α, IL-6 and MCP-1 in the supernatants were determined using ELISA kits.

Effect of DM on the LPS-Induced Macrophage Activation

The inflammatory reaction can be inhibited by dextromethorphan at less than 0.01 μM. The THP-1 cell treated with LPS at 1 Unit/ml in the presence of dextromethorphan for 24 hrs and the TNF-α and IL-6 released in the culture medium was measured with ELISA (FIG. 1). FIG. 1 shows effect of dextromethorphan treatment on the LPS-induced macrophage release of TNF-α (A) and IL-6 (B). THP-1 cell culture was pretreated for 1 hour with the indicated concentrations of dextromethorphan before stimulation with 100 ng/mL LPS. Supernatants were harvested at 24 hours for the measurement of TNF-α and IL-6. The results are expressed as mean±SD of 3 experiments.  $p<0.01$ and * $p<0.001$ are compared with the LPS-treated cultures.

Effect of Naloxone on the LPS-Induced Macrophage Activation

Figure 2:
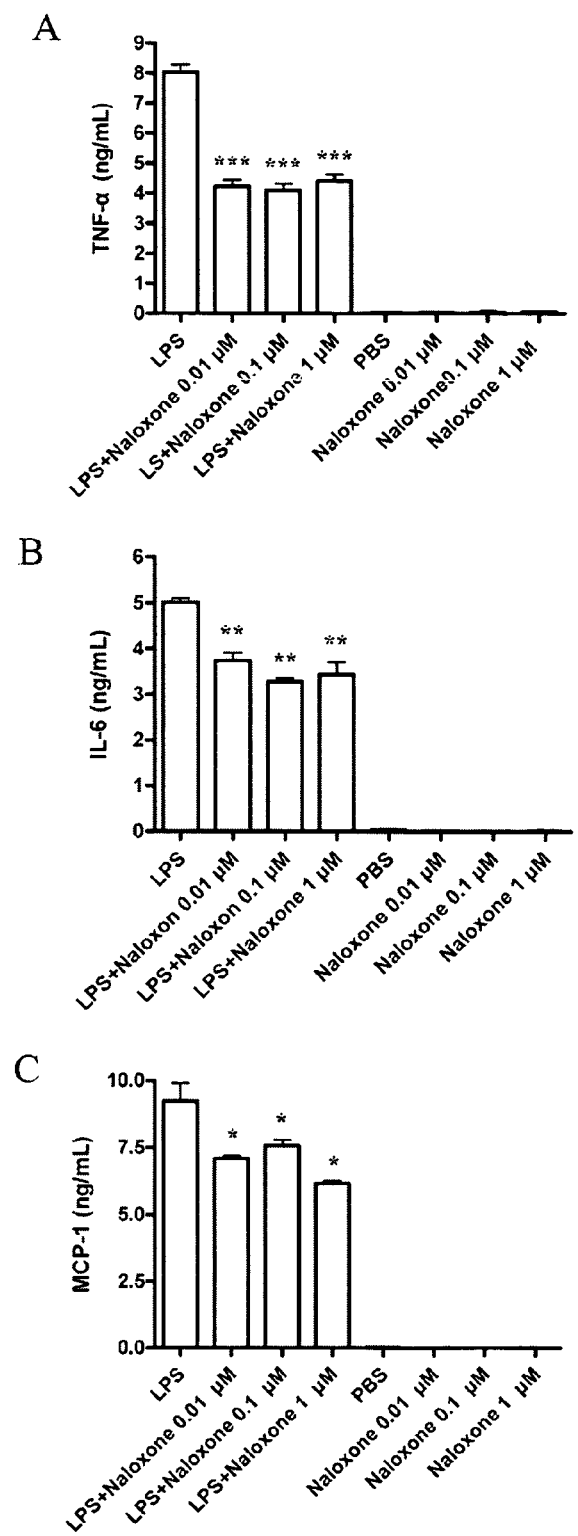
FIG. 2 shows the effect of naloxone treatment on LPS-induced macrophage release of TNFα (A), IL-6 (B) and MCP-1 (C).

Effect of naloxone treatment on the LPS-induced macrophage release of TNF-α (A), IL-6 (B) and MCP-1 (C). THP-1 cell culture was pretreated for 1 hour with the indicated concentrations of naloxone before stimulation with 100 ng/mL LPS. Supernatants were harvested at 24 hours for the measurement of TNF-α, IL-6 and MCP-1. The results are expressed as mean±SD of 3 experiments. * $p<0.05$;  $p<0.01$; * $p<0.001$ compared with the LPS-treated cultures (FIG. 2).

One skilled in the art readily appreciates that the present invention is well adapted to carry out the objects and obtain the ends and advantages mentioned, as well as those inherent therein. The cell lines, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A method of inhibiting growth of *Propionibacterium acnes* comprising:
    exposing *Propionibacterium acnes* to a composition comprising an effective amount of (+)-3-methoxy 17-methyl-9α, 13α, 14α-morphinan (dextromethorphan) or a salt thereof, and a pharmaceutically acceptable carrier, and thereby inhibiting the growth of *Propionibacterium acnes*.

2. The method of claim 1, prior to the exposing step further comprising the step of administering said composition to a patient in need thereof.

3. The method of claim 2, wherein the *Propionibacterium acnes* are exposed to a composition comprising a therapeutically effective amount of salt of dextromethorphan and a pharmacologically acceptable carrier.

4. The method of claim 3, wherein the *Propionibacterium acnes* are exposed to a composition comprising a therapeutically effective amount of dextromethorphan hydrobromide or dextromethorphan phosphate and a pharmacologically acceptable carrier.

5. A method of inhibiting growth of *Propionibacterium acnes* on the skin of a patient comprising:
    exposing *Propionibacterium acnes* on the skin of the patient to a composition comprising a therapeutically effective amount of dextromethorphan or salt thereof and a pharmaceutically acceptable carrier, and thereby inhibiting the growth of *Propionibacterium acnes* on the skin of the patient.

6. The method of claim 5, wherein the *Propionibacterium acnes* are exposed to a composition comprising a therapeutically effective amount of dextromethorphan hydrobromide or dextromethorphan phosphate and a pharmacologically acceptable carrier.

7. A method of inhibiting growth of *Propionibacterium acnes* for treating acne on the skin of a patient comprising the steps of:
    (a) administering to the skin of the patient a composition comprising a therapeutically effective amount of dextromethorphan or a salt thereof, and a pharmaceutically acceptable carrier;
    (b) exposing *Propionibacterium acnes* on the skin of the patient to the therapeutically effective amount of dextromethorphan or a salt thereof; and
    (c) inhibiting growth of the *Propionibacterium acnes*, and thereby treating acne on the skin of the patient.

8. The method of claim 7, wherein the administering step is replaced by: administering a composition consisting of a therapeutically effective amount of dextromethorphan and a pharmaceutically acceptable carrier.

9. The method of claim 7, wherein the administering step is replaced by: administering a composition consisting of a therapeutically effective amount of dextromethorphan salt and a pharmaceutically acceptable carrier.

10. The method of claim 7, wherein the composition comprises a therapeutically effective amount of dextromethorphan salt and a pharmaceutically acceptable carrier.

11. The method of claim 10, wherein the compositions comprises a therapeutically effective amount of dextromethorphan hydrobromide or dextromethorphan phosphate and a pharmaceutically acceptable carrier.

* * * * *